United States Patent [19]

Kaiser et al.

[11] Patent Number: 4,866,995

[45] Date of Patent: Sep. 19, 1989

[54] DEVICE FOR TAKING SAMPLES FROM A CATALYST BLOCK OF A CATALYTIC CONVERTER

[75] Inventors: Heinz Kaiser, Russelsheim; Andrea Köhler, Frankfurt; Werner J. Rühl, Langen, all of Fed. Rep. of Germany

[73] Assignee: General Motors Corporation, Detroit, Mich.

[21] Appl. No.: 245,604

[22] Filed: Sep. 19, 1988

[30] Foreign Application Priority Data

Nov. 6, 1987 [DE] Fed. Rep. of Germany ....... 8714787

[51] Int. Cl.$^4$ .............................................. G01N 1/04
[52] U.S. Cl. ................................................. 73/864.41
[58] Field of Search ........................ 73/864.41–864.45, 73/863.81, 863.82, 118.1; 83/919, 84, 167; 408/23

[56] References Cited

U.S. PATENT DOCUMENTS

| 319,282 | 6/1885 | Machol | 83/167 |
| 3,339,435 | 9/1967 | Heitz | 408/67 |
| 3,340,915 | 9/1967 | Passer | 408/67 |
| 3,492,875 | 2/1970 | Tonjes | 73/864.43 |
| 3,677,117 | 7/1972 | Cutter | 83/167 |
| 4,200,417 | 4/1980 | Hager et al. | 408/67 |
| 4,653,327 | 3/1987 | Varterasian et al. | 73/118.1 |

FOREIGN PATENT DOCUMENTS

| 0887733 | 12/1971 | Canada | 73/863.81 |
| 2404504 | 8/1975 | Fed. Rep. of Germany | 408/67 |
| 0956716 | 4/1964 | United Kingdom | 73/864.43 |

Primary Examiner—Robert R. Raevis
Attorney, Agent, or Firm—R. L. Phillips

[57] ABSTRACT

A device for taking samples from a catalyst block of a catalytic converter has a cutting tool rotatably mounted in a base plate that is surrounded by a collecting dish.

3 Claims, 2 Drawing Sheets

DEVICE FOR TAKING SAMPLES FROM A CATALYST BLOCK OF A CATALYTIC CONVERTER

TECHNICAL FIELD

This invention relates to taking samples from a catalyst block of a catalytic converter for a motor vehicle.

BACKGROUND OF THE INVENTION

To perform studies on exhaust catalysts, it is often necessary to take material samples from specified regions of the monolithic catalyst block for the purpose of subsequent chemical analysis. This can be done for example by the manufacturer within the framework of demonstrating the functional capacity of the catalyst during a type test. Such studies are also necessary to learn whether leaded fuel was used.

Until now, the catalyst block has been exposed, for the purpose of sample collection, by destroying the catalyst housing, followed by sample taking. This type of sampling leads to the destruction of the catalyst. Because of the material loss involved, it is also disadvantageous that no subsequent measurements on the catalyst are possible, since the latter is destroyed by the sampling process. Therefore, basic studies requiring repeated taking of samples after certain operating times are not performed.

SUMMARY OF INVENTION

The present invention offers a device that can repeatedly take samples from a catalyst block without destroying it. The device comprises a cutting tool rotatably mounted in a base plate and a collecting dish surrounding the tool for collecting the cuttings produced by the tool.

With such device, a sample can be taken from the catalyst block from both the front end and the rear end of the catalyst container by bringing the catalyst container into a vertical position and positioning the device from below. The quantity of material collected in the collecting dish in this way can be so small that it reduces the functional capacity of the catalyst only to a negligible degree. As a result, one can determine without destroying the catalyst whether it is still fully functional. In addition, by studying a sample, it can be found whether, for example, lead poisoning is responsible for inadequate exhaust purification. In addition, valuable information can be gained for the design and construction of exhaust catalysts by studying such nondestructively and repeatedly taken samples.

Sample materials from the interior of the catalyst block can be quickly obtained by the tool being a twist drill according to one advantageous version of the invention.

For studies of the catalyst material in the region of its surface on the front ends of the catalyst block, it is advantageous for the tool to be a face milling cutter.

The device has an especially simple configuration when the collecting dish is formed with a coaxial opening and a twist drill is pushed onto it. An ordinary twist drill can be used for such a device.

The mounting of a face milling cutter on the device can be done in a very simple way by forming the face milling cutter on the end face of a socket which can be mounted on a twist drill and securing it against rotation by a radial clamping screw.

The device is even further simplified when the tool is provided with a rod penetrating the base plate that is capable of rotary and axial motion in it by means of a bearing bush, this rod having a hand grip on the side of the base plate facing away from the tool for turning the rod and thus the tool.

The slipping of the rod out of the base plate can be prevented simply by providing a clamping ring fixed by a clamping screw on the rod above the bearing bush.

The device can be mounted very simply on an ordinary catalyst container by the base plate being adapted for seating on an end face flange of a catalyst container and having a centering disk that can be inserted into the flange opening, through which the rod with the tool is guided.

Samples can be taken at a precisely defined point at various times if necessary by a fixing pin being provided in the base plate for positioning the base plate in a flange boring of the catalyst container.

It is also possible to take several samples from precisely defined places by the fixing pin being optionally insertable into several borings arranged on a common reference circle.

BRIEF DESCRIPTION OF THE DRAWINGS

These and other objects, advantages and features of the present invention will become more apparent from the following description and drawing in which.

DESCRIPTION OF PREFERRED FORM OF INVENTION

Figure 1:
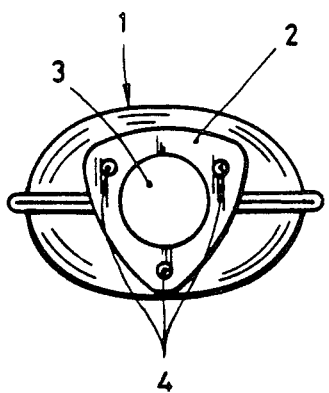
FIG. 1 is a front view of a motor vehicle exhaust system catalytic converter in which the device according to the innovation can be used.

FIG. 1 shows a catalytic converter 1 with a flange 2 which has a flange opening 3 through which the exhaust gas flows. A total of three flange borings 4 are provided in the flange which serve to fix the catalyst 1 in an exhaust system (not shown).

Figure 2:
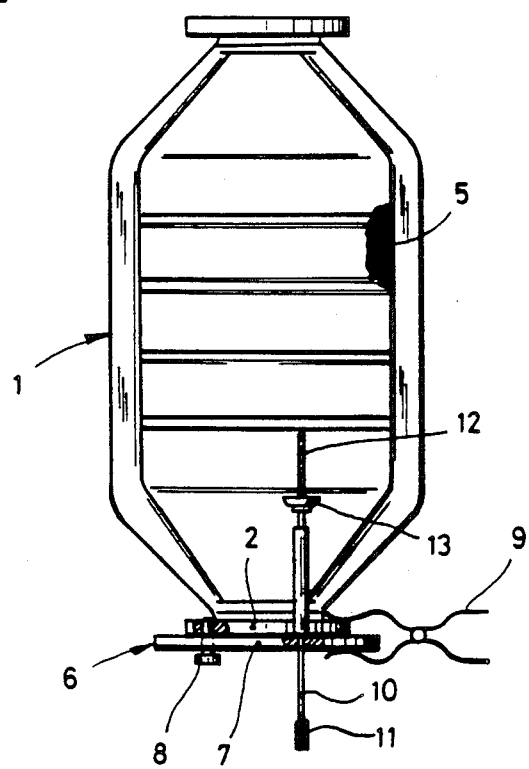
FIG. 2 is a schematic longitudinal section through the catalytic converter with the device mounted on it.

FIG. 2 shows the catalytic converter 1 in the vertical position in which it must be brought to take a sample. In the interior of the converter 1, a monolithic catalyst block 5 is shown. A device 6 is set with a base plate 7 against the flange 2 from below and is held in this position by a fixing pin 8, which intrudes into one of the flange borings 4 (FIG. 1), and by a clamp 9. A rod 10 extends downwardly out of the base plate 7 with a handle 11 which passes through the base plate 7 into the converter 1 and carries a tool 12 there, in this version a twist drill. This tool 12 is surrounded by a collecting dish 13. If one twists the handle 11 while simultaneously exerting axial pressure, the tool 12 drills increasingly into the catalyst block 5. The cuttings produced as a result drop into the collecting dish 13 and can be removed as material samples after the device 6 is lifted off.

Figure 3:
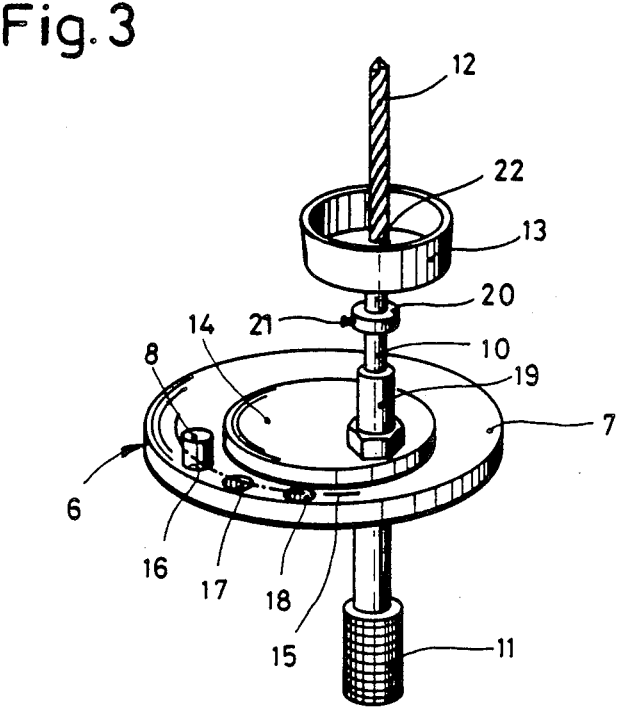
FIG. 3 is a three-dimensional view of the device according to the innovation.

FIG. 3 shows the configuration of the device 6 more precisely. One sees that the base plate 7 is graduated upwardly so that a circular centering disk 4 is produced which fits precisely into the flange opening 3. The base plate 7 outside the centering disk 14 on a common reference circle 15 has three borings 16, 17, 18. In boring 16, a fixing pin 8 intruding into one of the flange borings 4 is inserted. Instead of this, however, it can also be set in borings 17 or 18 if a sample is to be taken from a different place in the catalyst block 5.

FIG. 3 also shows that the rod 10 passes through a bearing bush 19 screwed onto the top of the centering disk 14. Above this bearing bush 19 on the rod 10, a clamping ring 20 is held by means of a radially directed clamping screw 21 so that the rod 10 cannot slide down out of the bearing bush 19. Above the clamping ring 20 is the collecting dish 13 which in this version has a coaxial boring 22 which passes through the tool 12 designed as a twist drill. The collecting dish 13 can also be held on the tool 12 by a clamping screw (not shown).

Figure 4:
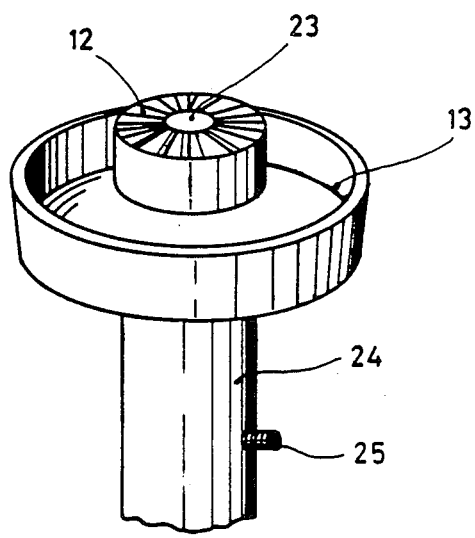
FIG. 4 is a three-dimensional view of a milling tool of the device according to the innovation.

In FIG. 4, a face milling cutter is shown as the tool which has a central hollowed out region 23 and is provided on the end face with a socket 24. This socket 24 is so designed that it can be pushed onto the tool 12 designed as a twist drill and be secured by means of a clamping screw 25. Precisely as in the case of the version described above, the tool designed as a face milling cutter is surrounded by a collecting dish 13 which in this case, however, is formed as a single piece with the socket 24 and the tool 12.

We claim:

1. Sampling device for taking samples from a catalyst block mounted in a catalytic converter wherein the converter has an end flange with an opening through which exhaust gas flows to or from the catalyst block, said sampling device comprising a base plate adapted for center mounting on said end flange by means of a centering disc insertable into said opening, a cutting tool rotatably mounted to said base plate in an off center position relative to said flange opening and extending through said centering disc and adapted to extend to said catalyst block for cutting contact therewith, a collecting dish mounted together with said tool on said base plate and adapted to extend about and below an end of said tool beneath said catalyst block for collecting cuttings from said catalyst block produced by said tool.

2. Sampling device according to claim 1 further characterized in that the base plate is provided with a fixing pin for positioning the base plate relative to the catalyst block by insertion in a fastening bore in the end flange.

3. Sampling device according to claim 1, further characterized in that the base plate is provided with a fixing pin that can optionally be inserted in several fastening bores in the base plate arranged in a common reference circle.

* * * * *